(12) United States Patent
Peng et al.

(10) Patent No.: US 8,097,441 B2
(45) Date of Patent: Jan. 17, 2012

(54) ETHANOL PRODUCTION FROM GRAMINACEOUS PLANTS BY USING IMMOBILIZED CARBOHYDRATE HYDROLASES ON NANOPARTICLES

(76) Inventors: Kou-Cheng Peng, Taoyuan (TW); Shuo-Ting Hung, Xindian (TW); Hong-Ming Lin, Xinzhuang (TW); Wen-Chang Chen, Taipei (TW); Chaur-Tsuen Lo, Huwei (TW); She-Huang Wu, Taipei (TW)

(*) Notice: Subject to any disclaimer, the term of this patent is extended or adjusted under 35 U.S.C. 154(b) by 887 days.

(21) Appl. No.: 12/129,964

(22) Filed: May 30, 2008

(65) Prior Publication Data

US 2008/0299631 A1    Dec. 4, 2008

Related U.S. Application Data

(60) Provisional application No. 60/941,096, filed on May 31, 2007.

(51) Int. Cl.
*C12P 7/10* (2006.01)
*C12M 1/00* (2006.01)
*C12N 13/00* (2006.01)

(52) U.S. Cl. .................... 435/165; 435/174; 435/191.1; 977/773

(58) Field of Classification Search .............. 435/165, 435/174, 291.1; 977/773
See application file for complete search history.

(56) References Cited

U.S. PATENT DOCUMENTS

| 7,074,603 | B2 | 7/2006 | Verser et al. |
| 7,138,257 | B2 | 11/2006 | Galli et al. |

*Primary Examiner* — Herbert J Lilling
(74) *Attorney, Agent, or Firm* — WPAT, P.C.; Anthony King

(57) ABSTRACT

The present invention relates to a carbohydrate hydrolase-immobilized magnetic nanoparticle; a method of preparing ethanol from graminaceous plants and a continuous system of preparing ethanol.

20 Claims, 9 Drawing Sheets

ETHANOL PRODUCTION FROM GRAMINACEOUS PLANTS BY USING IMMOBILIZED CARBOHYDRATE HYDROLASES ON NANOPARTICLES

FIELD OF THE INVENTION

The present invention relates to a carbohydrate hydrolase-immobilized magnetic nanoparticle; a method of preparing ethanol from graminaceous plants and a continuous system of preparing ethanol.

BACKGROUND OF THE INVENTION

U.S. Pat. No. 7,138,257 discloses method for producing ethanol by using corn flours. U.S. Pat. No. 7,074,603 discloses process for producing ethanol from corn dry milling.

Traditional technology utilizes industrial enzymes to decompose high-molecular-weight carbohydrate into small molecules (for producing ethanol in a fermentor) in the first bioreactor step. This process requires tremendous amount of industrial enzymes which is very expensive. These enzymes are sensitive to environmental changes which will increase the processing cost and decrease the enzyme activity and ethanol production rate.

Pretreatment of the raw material (cereals) includes wet mill and dry mill. Wet mill is performed by placing cereals in water, incubating with $H_2SO_4$ at pH 5.8 for 48 hours, neutralizing with bases, and then applying lots of industrial enzymes to decompose cereals into oligosaccharide. This procedure increases the handling cost of raw material processing and environmental pollution. Cereals for dry mill treatment need to be ground into finer particles for enzymatic reaction which increases the difficulty of material processing. Also, high heat generated during the grinding process may react with cereals and generate toxic substances easily.

Fermentation broth needs to be taken out for sterilization before placing it into ethanol fermentor. This non-continuous handling step adds extra cost because of operation risk and manpower.

Take corn as an example, it requires six steps to generate corn flours. More energy input is involved as well as less raw material is recovered due to multiple steps. Therefore, production rate is decreasing and cost is increasing.

Traditional technology utilizes economic crops as raw material, such as rice starch, corn starch, or starch from other economic crops which increases the manufacturing cost.

Base on the nanotechnology, many state-of-art inventions with immense industrial valued such as the magnetic nanoparticles have been developed.

To apply to Biotechnology, the magnetic nanoparticles have to disperse or suspense stably in water solution. But the compositions of the nanomagnetic particles are $Fe_3O_4$, $MnFe_2O_4$ and $CoFe_2O_4$ etc. monocrystal which are insoluble in water. So, hydrophilic surfactant activators are layered on the surface of the magnetic nanoparticles so that they disperse or suspense stably in water solution.

The important character of the magnetic nanoparticles is its particle size similar with biomolecules. So, designated biomolecules own magnetic character by binding to the surface-modified magnetic nanoparticles. Once the magnetic field is applied to the system, the dipole generated in the nanomagnetic particles along the direction of magnetic field. Currently, this technology has been applied to the cell sorting, ELISA, gene transfer, and others.

The magnetic nanoparticles isolation has many advantages over the others isolation: easy isolation steps in short term and high efficiency and excellent specificity. Currently, this technology has been applied to the cell sorting, ELISA, gene transfer, and others. This technology can also apply to the proteins including enzymes, and other biomolecules that great impact happen onto the biochemical industry and academia.

SUMMARY OF THE INVENTION

The present invention discloses a carbohydrate hydrolase-immobilized magnetic nanoparticle.

The present invention also provides a method of preparing ethanol from graminaceous plants by using the carbohydrate hydrolase-immobilized magnetic nanoparticles.

The present invention further discloses a continuous system of preparing ethanol.

DETAILED DESCRIPTION OF THE INVENTION

Figure 1:
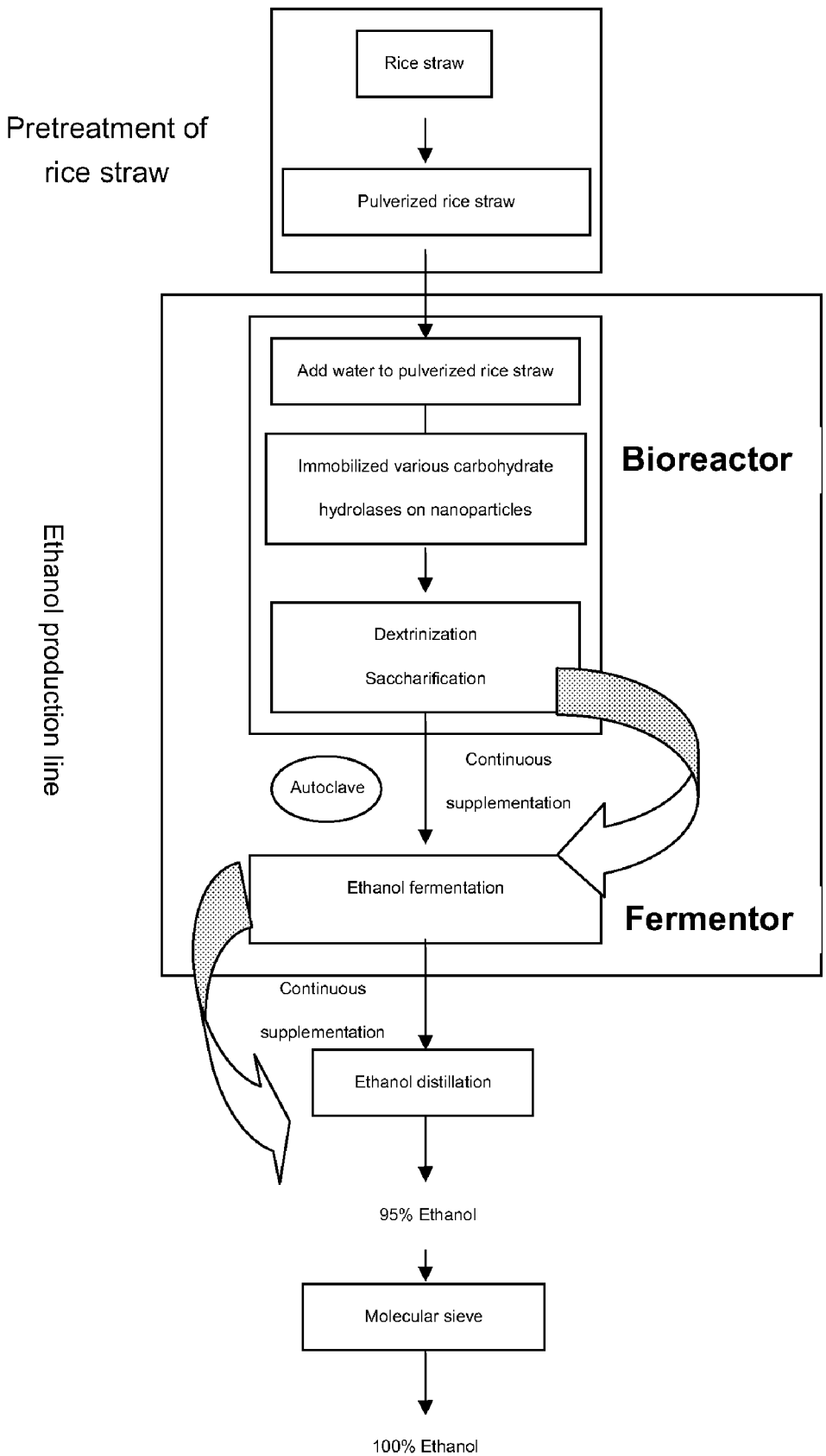
FIG. 1 shows a typical flow chart for preparing biofuel.
Figure 2:
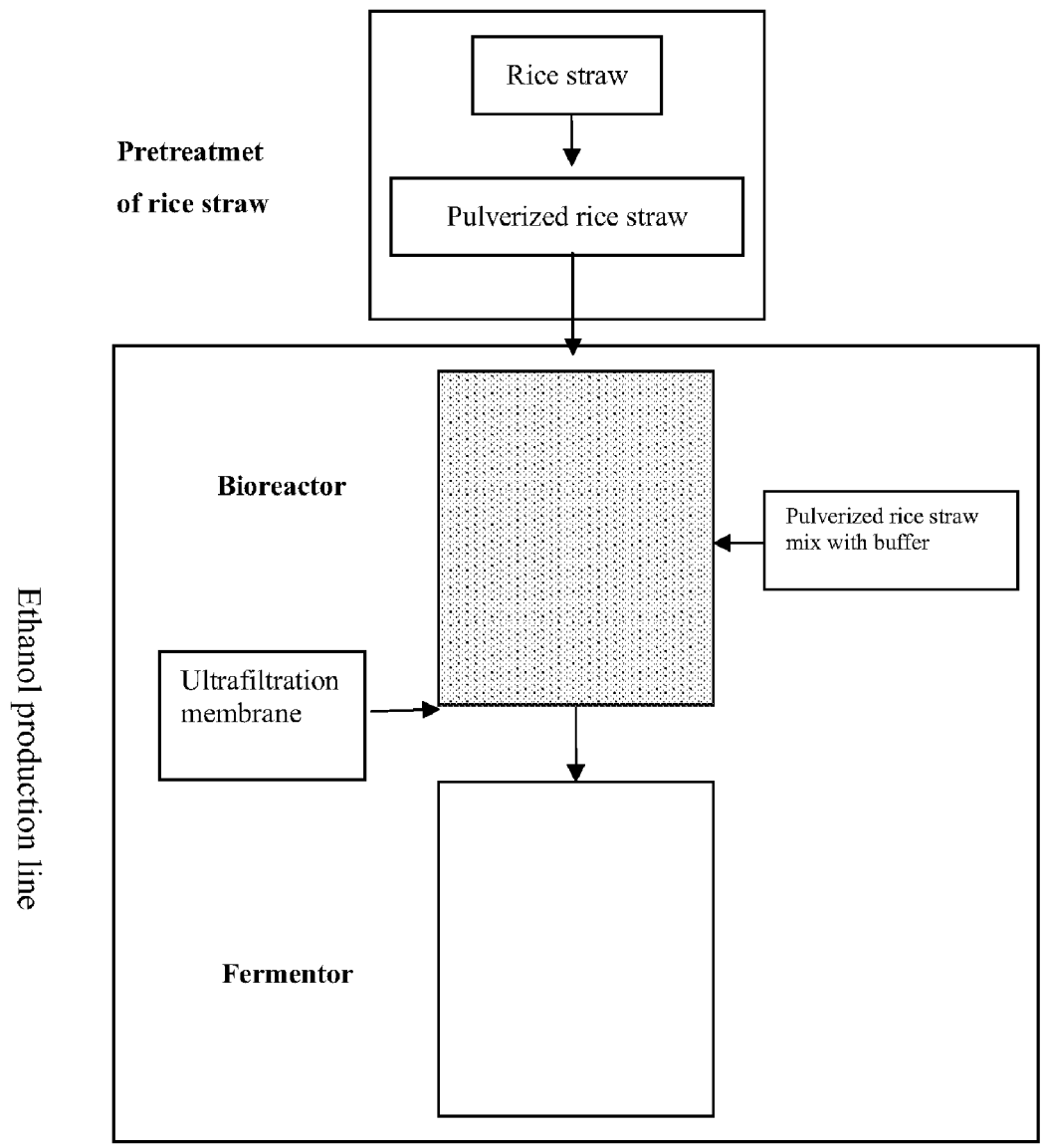
FIG. 2 shows the process of adding pulverized rice straw mixed with buffer into a bioreactor of FIG. 1.
Figure 3:
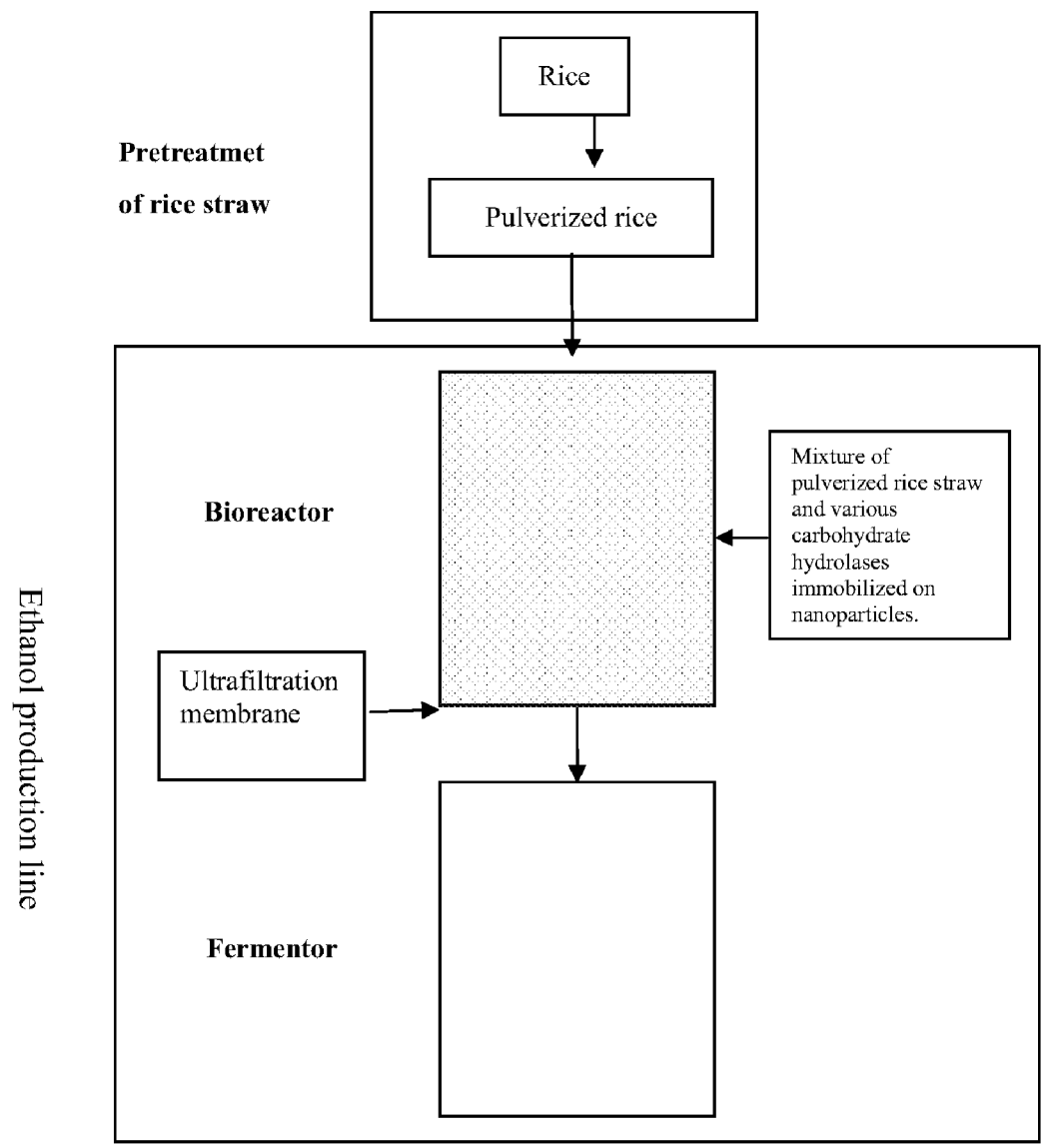
FIG. 3 shows adding the mixture of pulverized rice straw and various carbohydrate hydrolases immobilized on nanoparticles into the bioreactor of FIG. 1.
Figure 4:
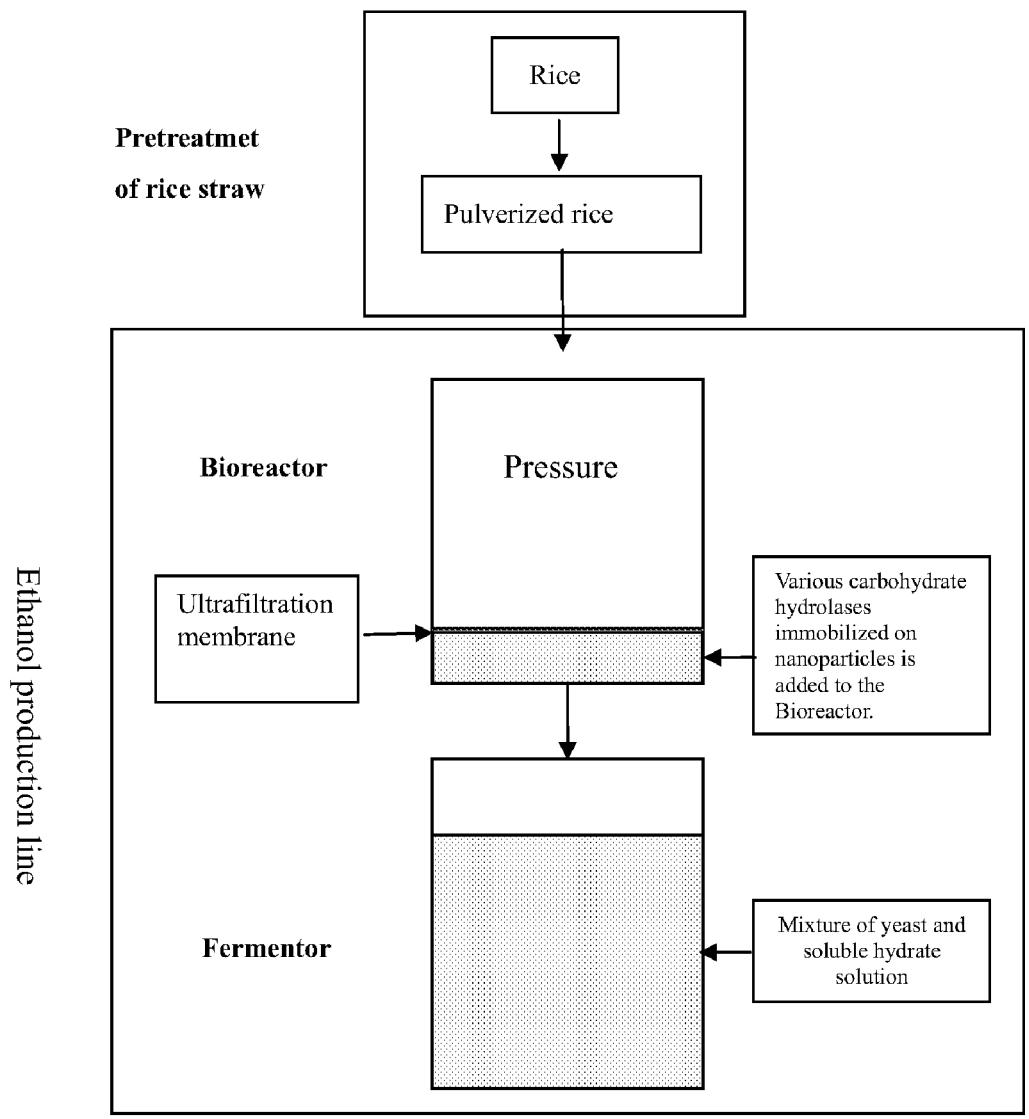
FIG. 4 shows adding the mixture of yeast an soluble hydrate solution into the fermentor of FIG. 1.
Figure 5:
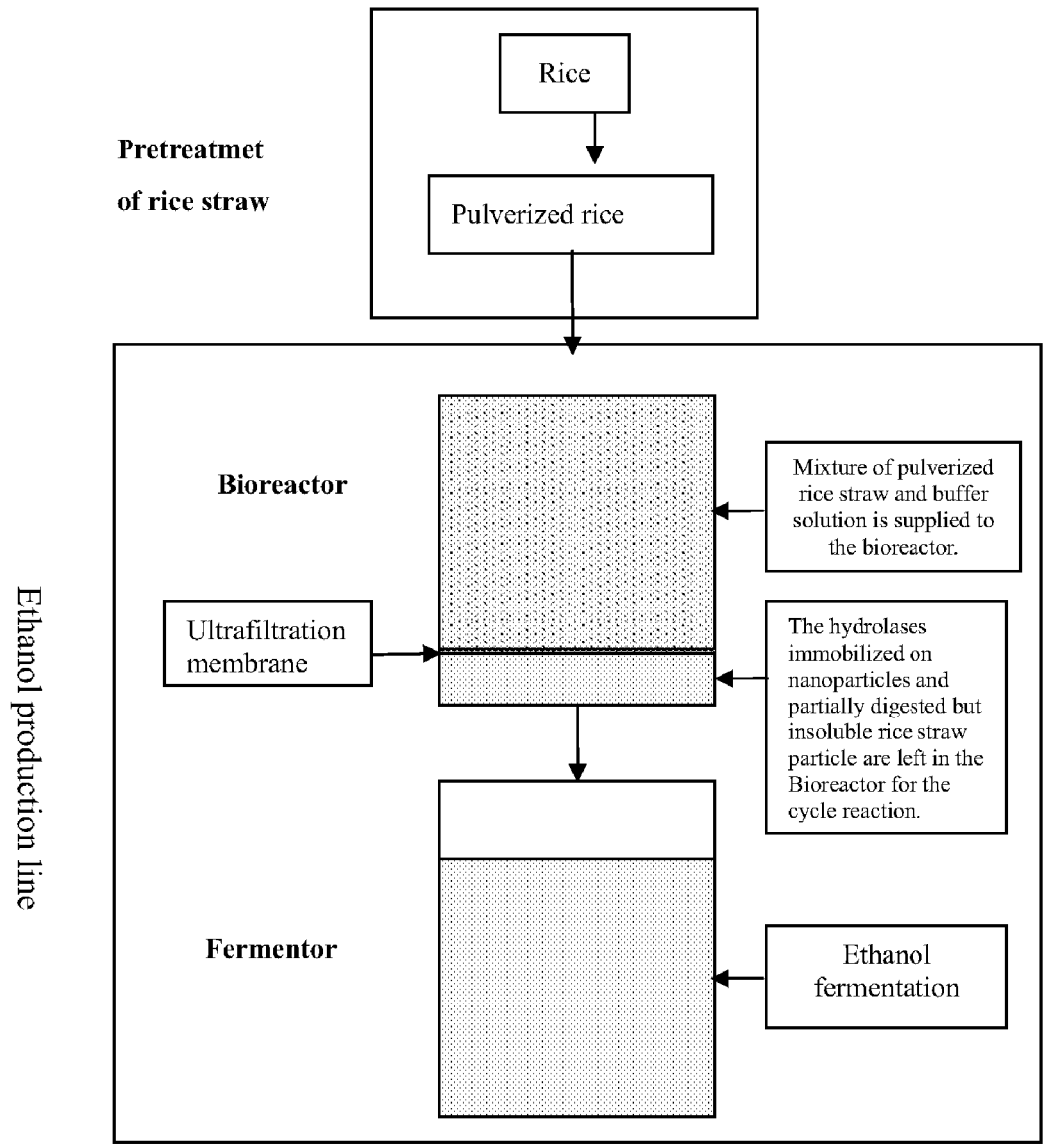
FIG. 5 shows that the partially digested but insoluble rice straw particle are filtrated by ultrafiltration membrane and left in the bioreactor for the cycle reaction.
Figure 6:
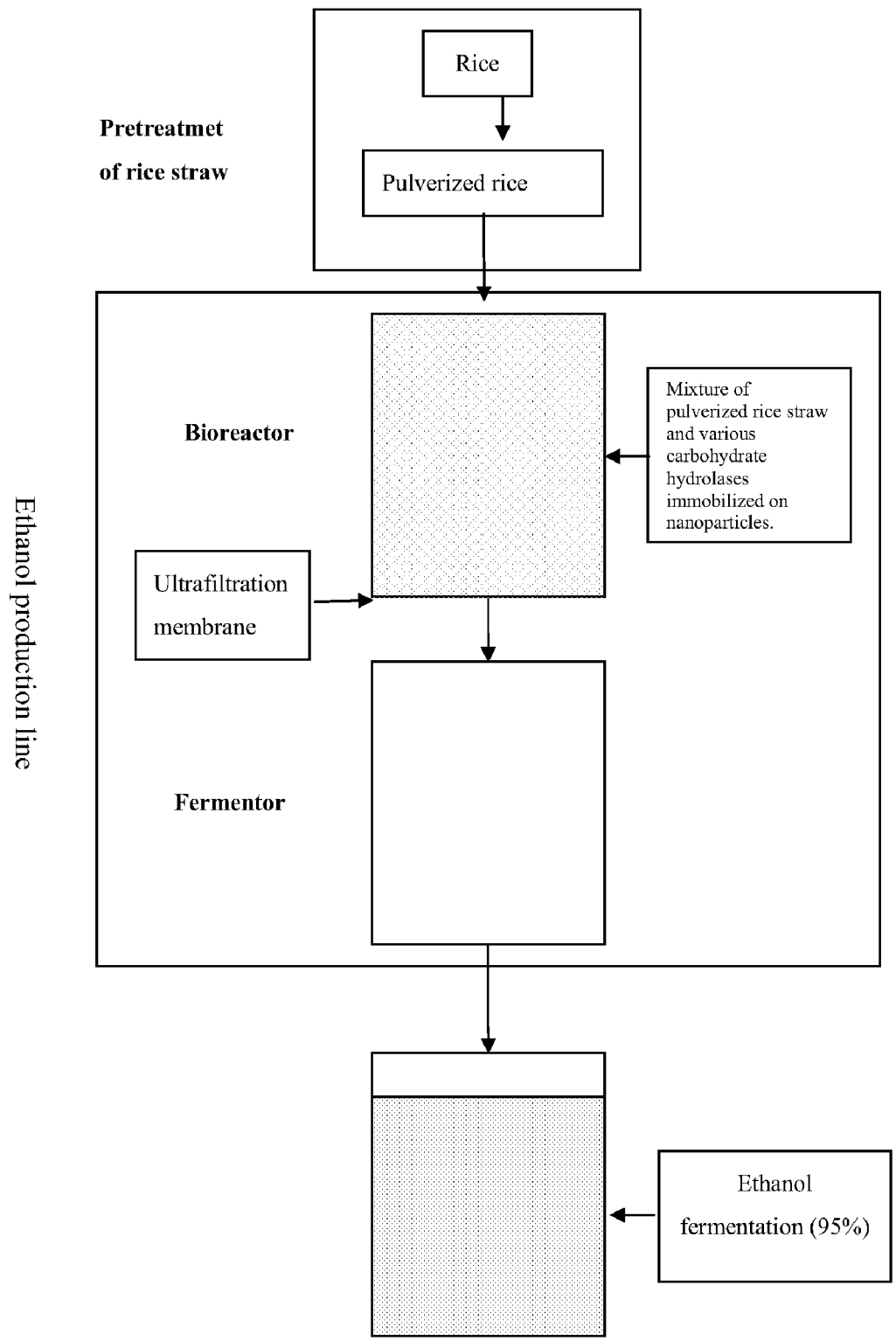
FIG. 6 shows that ethanol was produced by fermentation in the fermentor of FIG. 1.
Figure 7:
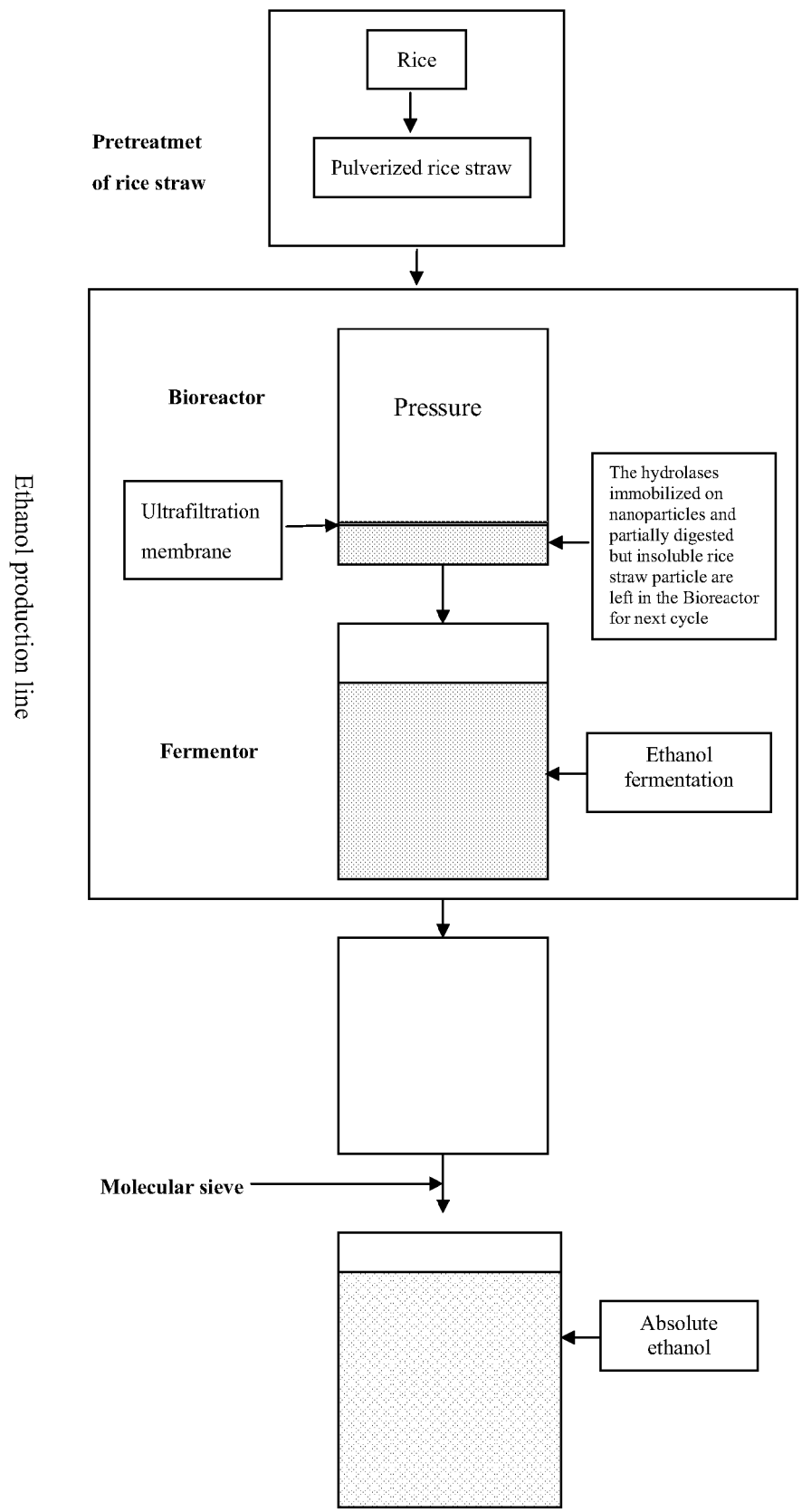
FIG. 7 shows the absolute ethanol can be obtained by molecular sieve.
Figure 8:
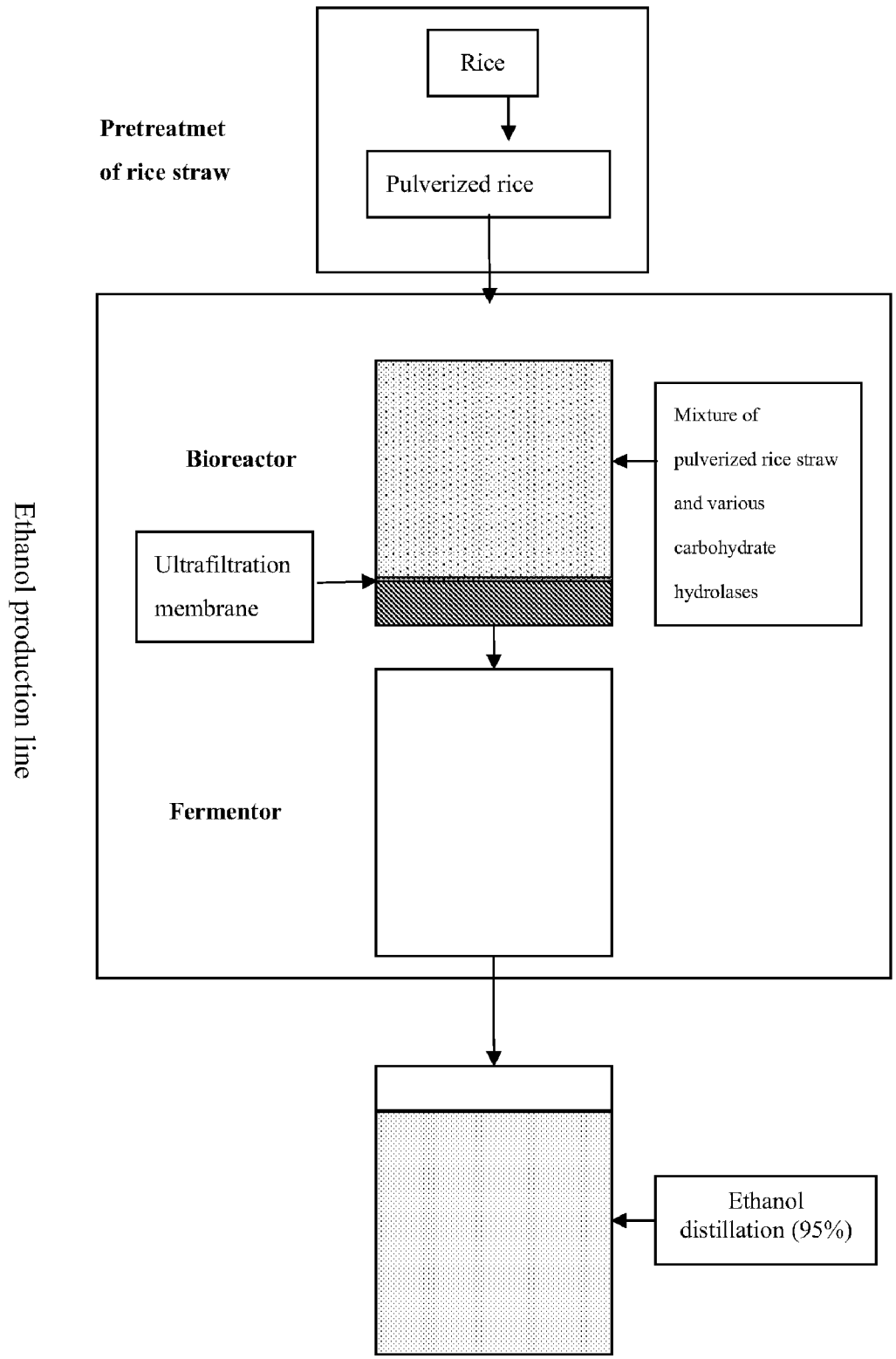
FIG. 8 shows the 95% ethanol can be obtained from the fermentor by distillation.
Figure 9:
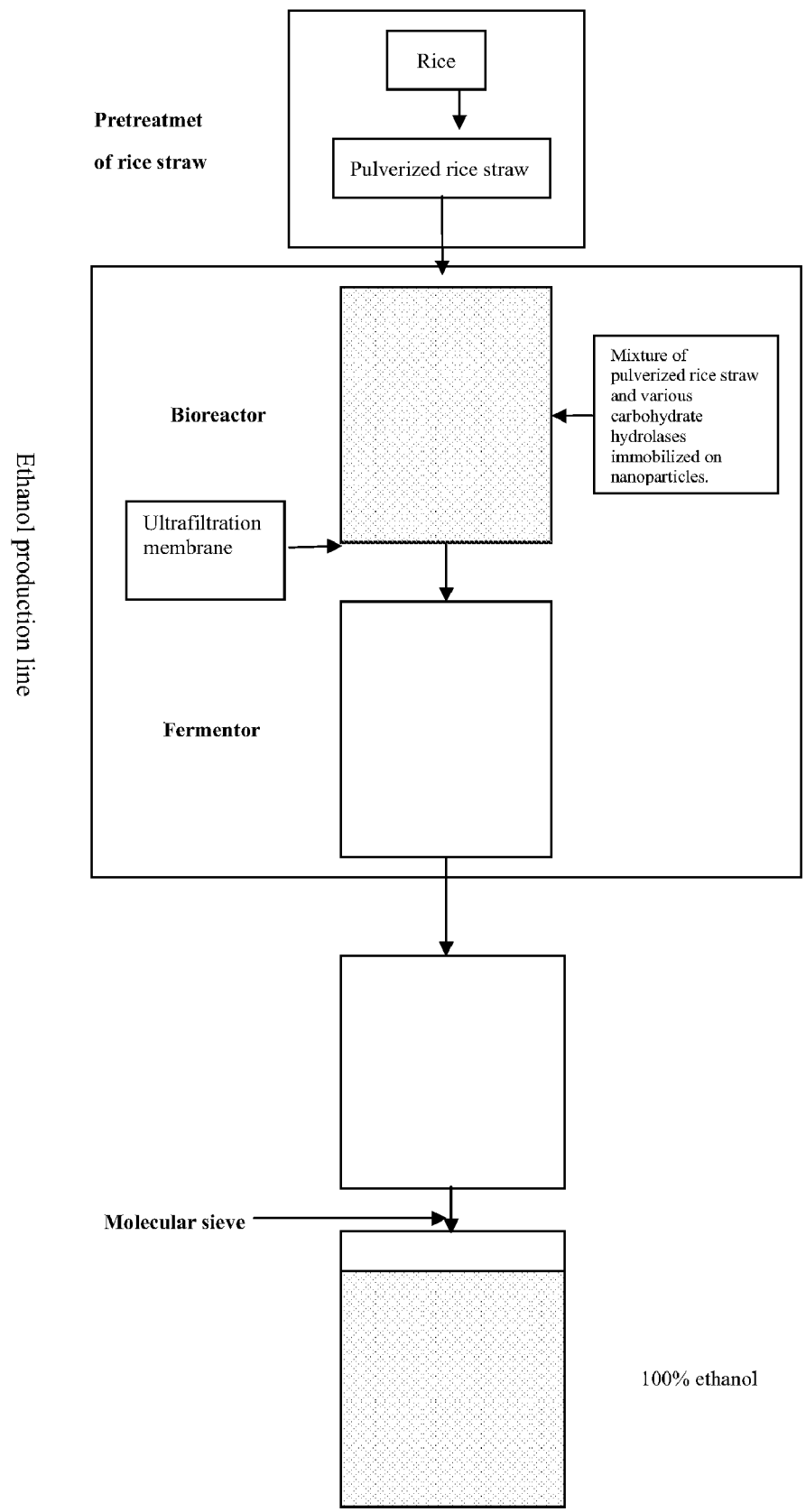
FIG. 9 shows the absolute ethanol can be obtained by molecular sieve.

The term "Hydrolase" used herein is intended to mean EC 3.2.1.xxx: Glycosidases, i.e. enzymes hydrolysing O- and S-glycosyl compounds.

To turn rice straw, seeds and/or stems of graminaceous plants, and/or fiber into ethanol by various immobilized carbohydrate hydrolases on magnetic nanoparticles.

The present invention utilizes various immobilized carbohydrate hydrolases on magnetic nanoparticles to replace partially purified enzymes or pure enzymes but both are not immobilized. The immobilized carbohydrate hydrolases on magnetic nanoparticles are reusable for decomposing carbohydrate over time with low cost.

The present invention discloses carbohydrate hydrolase-immobilized magnetic nanoparticle, comprising (i) a core having a coated surface, and
(ii) a plurality of carbohydrate hydrolase, wherein the carbohydrate hydrolase is covalently coupled to the coated surface.

In preferred embodiment of the present invention, the magnetic nanoparticle is $Fe_3O_4$; the coated surface is a cross-linker like carbodiimide and the carbohydrate hydrolase is cellulase.

In addition, this invention also discloses a method of preparing ethanol from graminaceous plants by using the carbohydrate hydrolase-immobilized magnetic nanoparticle, comprising:

(i) mixing buffer solution with a graminaceous plant to form a mixture;
(ii) placing the mixture into a bioreactor;
(iii) adding the carbohydrate hydrolase-immobilized magnetic nanoparticle into a bioreactor;
(iv) transferring the soluble hydrolysate into ethanol fermentor;
(v) adding ethanol fermentation yeast into the fermentor to produce ethanol;
(vi) distilling ethanol till 95%, and
(vii) purifying ethanol by molecule sieve.

In preferred embodiment of the present invention, the method further comprises recycling the immobilized carbohydrate hydrolases on magnetic nanoparticles for next carbohydrate hydrolysis.

The raw material for ethanol biosynthesis is rice straw. The carbohydrate hydrolase-immobilized magnetic nanoparticles can decompose high-molecular-weight carbohydrate from rice straw into low-molecular-weight oligosaccharide and glucose for ethanol production by ethanol fermentation yeast.

The raw material of this method is not limited to cellulose, even current waste of non-economical crops and stem of economical crops, straw of rice, corn, wheat, oat and other graminaceous plants are suitable sources. If the economic product as fruit cellulose of these graminaceous plants can be used as raw material, the ethanol can be generated efficiently.

The present invention produces ethanol as a target product as well as other byproducts, such as semi-fermented stem and/or fiber which can be used as excellent livestock feed and biocontrol reagent with further development.

In particular, the present invention has efficiently transform waste of non-economic crops (stem and/or fiber) into ethanol by carbohydrate hydrolases-immobilized magnetic nanoparticles. Accordingly, the present invention can be applied in ethanol production industry, biofuel production industry and food science industry.

The present invention further discloses a continuous system of preparing ethanol, comprising:
(i) a bioreactor with filtration membrane, wherein the bioreactor comprises the carbohydrate hydrolase-immobilized magnetic nanoparticles for decomposing high-molecular weight carbohydrate into oligosaccharide, and
(ii) an ethanol fermentor connected with bioreactor by connected pipe, wherein the ethanol fermentor comprises microorganism for producing ethanol.

In preferred embodiment of the present invention, the microorganism is yeast.

The system also comprises ethanol distillation tank connected with ethanol fermentor for ethanol production.

The system further comprises magnetic field supplier to enhance the recycling of the carbohydrate hydrolase-immobilized magnetic nanoparticle.

The filtration membrane in a bioreactor is used to separate the soluble hydrolysate and the carbohydrate hydrolase-immobilized magnetic nanoparticle and partially digested but insoluble rice straw particle by applying pressure.

Connected pipe can transfer newly generated oligosaccharides from bioreactor to fermentor directly and autoclave it simultaneously (FIG. 1) for ethanol production. Further distillation can recover 95% ethanol and molecular sieve can recover 100% ethanol.

Connected pipe can continuously transfers newly generated oligosaccharides from bioreactor to fermentor for ethanol production with pre-existing yeast. This continuous process can increase ethanol production rate, reduce handling cost, and increase the amount of product.

The connected pipe can directly connect bioreactor and fermentor to establish a continuous ethanol fermentation system and in-place cleaning and sterilization, if required, can be done simultaneously.

Fermentation broth in the fermentor can be taken out continuously for ethanol production by distillation.

EXAMPLE

Example 1

Immobilization on Nanomagnetic Particles

Buffer A:
3 mM phosphate buffer were prepared as buffer A: $Na_2HPO_4$, 0.213 g in 500 ml $ddH_2O$ and 0.234 g $NaH_2PO_4.2H_2O$ in 500 ml $ddH_2O$ were prepared. Then, 250 ml of each was mixed and pH was adjusted to 6.

Immobilization:
100 mg nanomagnetic particle in 2 ml buffer A was sonicated before 0.5 ml carbodiimide was added and well mixed. Cellulase, 4U/ml, 2.5 ml was added and well mixed, then sonication for 30 min. The magnetic field was applied to the mixture and immobilized enzyme was collected. Cellulase remained in solution was determined by protein concentration determination such as Bio-Rad Protein Assay, Bradford or others. The immobilization efficiency was determined by minus the remained protein concentration in the solution to the initial protein concentration.

Collected cellulase-immobilized-magnetic nanoparticles was rinsed once with buffer A, once with $ddH_2O$, and then resuspended in 6 ml $ddH_2O$, keep in 4° C. before used.

Activity of Cellulase-Immobilized-Magnetic Nanoparticles:
(1) Mixed 0.2 ml cellulase-immobilized-magnetic nanoparticles with 1 ml 1.5% carboxymethylcellulose and incubated 50° C., 10 min. The supernatant was collected by applying magnetic bar to the reaction mixture that the cellulase-immobilized-magnetic nanoparticles were retained in bottom of the container. The protein concentration in the supernatant was determined by the Bio-Rad Protein Assay.

(2) The cellulase-immobilized-magnetic nanoparticles that retained in bottom of the container were rinsed twice with 4 ml buffer A. Applied magnetic bar to decant the rinsed buffer then remove the magnetic bar. 1 ml 1.5% CMC solution was added to the cellulase-immobilized-magnetic nanoparticles for 10 min, 50° C. Again a magnetic field was applied to retain the cellulase-immobilized- magnetic nanoparticles and the supernatant was collected. The amount of reducing sugar in the supernatant was determined by DNS method. The protein concentration was determined by the Bio-Rad Protein Assay.

Results:

TABLE 1

| No. | $Fe_3O_4$ (mg) | Cellulase (mg) | $A_{595nm}$ | | Retained protein of the supernatant mg) | The immobilization efficiency (%) |
|---|---|---|---|---|---|---|
| 1 | 100.1 | 0.361 | 0.348 | ±0.008 | 0.0326 | 91 |
| 2 | 100.3 | | 0.340 | ±0.006 | | |
| 3 | 100.3 | | 0.301 | ±0.011 | | |
| 4 | 100.2 | | 0.275 | ±0.006 | | |
| 5 | 100.4 | | 0.281 | ±0.004 | | |
| Mean value | 100.3 | 0.361 | 0.309 | | | |

TABLE 2

| No. | $Fe_3O_4$ (mg) | Cellulase activity (U) | $A_{570nm}$ | | $1_{st}$ retained enzyme activity (U) | $1_{st}$ retained enzyme activity (%) |
|---|---|---|---|---|---|---|
| 1 | 100.1 | 31.4 | 0.986 | ±0.009 | 21 | 31.4/21 = 66.9 |
| 2 | 100.3 | | 0.953 | ±0.014 | | |
| 3 | 100.3 | | 1.007 | ±0.013 | | |
| 4 | 100.2 | | 1.012 | ±0.005 | | |
| 5 | 100.4 | | 0.984 | ±0.007 | | |
| Mean value | 100.3 | | 0.988 | | | |

TABLE 3

| No. | $Fe_3O_4$ (mg) | $1_{st}$ retained enzyme activity (U) | $A_{570nm}$ | | $2_{nd}$ retained enzyme activity (U) | $2_{nd}$ retained enzyme activity (%) |
|---|---|---|---|---|---|---|
| 1 | 100.1 | 21 | 0.483 | ±0.013 | 9.08 | 9.08/21 = 43.2 |
| 2 | 100.3 | | 0.479 | ±0.007 | | |
| 3 | 100.3 | | 0.461 | ±0.007 | | |
| 4 | 100.2 | | 0.420 | ±0.017 | | |
| 5 | 100.4 | | 0.409 | ±0.007 | | |
| average | 100.3 | | 0.450 | | | |

As showed in table 1-3, the sum of the cellulase-immobilized-magnetic nanoparticles activities of two consecutive reactions is 110.1% which is higher than the cellulase itself without immobilized. This is evidence the recycle of cellulase-immobilized-nanomagnetic particles system has higher efficiency and more output generated.

Example 2

The ethanol production procedure from rice straw by using carbohydrate hydrolase-immobilized magnetic nanoparticles and yeast is outlined as follows:
a. Collect dry rice straw on the field and grind it into pieces;
b. Mix buffer with pulverized rice straw, and place it into bioreactor after properly sterilized;
c. Add carbohydrate hydrolase-immobilized magnetic nanoparticles into culture;
d. Examine the activity of carbohydrate hydrolase and the amount of reducing sugars;
e. Remove partially degraded but insoluble pulverized rice straw (product A) from culture (product B) by connected pipe;
f. Place product B into ethanol fermentor, and add ethanol production yeast into the fermentor;
g. Determine ethanol content of the fermentor by an ethanol detector;
h. Recover 190 proof ethanol by distillation;
i. Repeat step e to h; and
j. Recover 200 proof ethanol by molecular sieve.

Example 3

Preparation of Biofuel

A. Pretreatment of Rice Straw, or Likewise
1. Rice straw dehydrated.
2. Pulverized the dried rice straw.
B. Bioreactor
1. Pulverized rice straw is applied to the bioreactor.
2. Buffer solution is supplied to the bioreactor.
3. Carbohydrate hydrolase-immobilized magnetic nanoparticle is added to the Bioreactor.
4. Optimal temperature is set during the hydrolysis and glucose is monitor in situ.
5. Pressure is applied to the bioreactor so that soluble hydrolysate passes through filtration membrane and transfer to a fermentor for further ethanol fermentation.
6. The carbohydrate hydrolase-immobilized magnetic nanoparticle and partially digested but insoluble rice straw particle left in the bioreactor will be further used for cycle reactions.
C. Cycle Reaction
1. Repeat Step A
   A. Pretreatment of Rice Straw, or Likewise
   (1) Rice straw dehydrated
   (2) Pulverized the dried rice straw.
2. Repeat Step B
   B. Bioreactor
   (1) New pulverized rice straw and buffer solution are applied to the bioreactor where the carbohydrate hydrolase-immobilized magnetic nanoparticle and partially digested but insoluble rice straw particle are left
   (2) Optimal temperature is set during the hydrolysis and glucose is monitor in situ.
   (3) Pressure is applied to the bioreactor so that soluble hydrolysate passes through filtration membrane and transfer to a fermentor for further ethanol fermentation.
   (4) The hydrolases immobilized on magnetic nanoparticles and partially digested but insoluble rice straw particle are left in the Bioreactor for next cycle reaction
D. Ethanol Fermentation
1. The soluble hydrolysates that pass through filtration membrane and transfer to the fermentor is treated with ethanol production yeast in optimal temperature, pH, and reaction time while the ethanol production is monitored in situ or analyzed in Biochemical methods.
2. An aliquot of yeast containing culture is extracted and keep for the next fermentations.
3. The culture is distilled to obtain 95% ethanol.
E. Absolute Ethanol Production
1. 100% ethanol is obtained by molecular sieve.

What is claimed is:

1. A carbohydrate hydrolase-immobilized magnetic nanoparticle, comprising:
   (i) a magnetic nanoparticle having a coated surface, and
   (ii) a plurality of carbohydrate hydrolase, wherein the carbohydrate hydrolase is covalently coupled to the coated surface.
2. The carbohydrate hydrolase-immobilized magnetic nanoparticle according to claim 1, wherein the magnetic nanoparticle is $Fe_3O_4$.
3. The carbohydrate hydrolase-immobilized magnetic nanoparticle according to claim 1, wherein the coated surface is a cross-linker.
4. The carbohydrate hydrolase-immobilized magnetic nanoparticle according to claim 3, wherein the cross-linker is carbodiimide.
5. The carbohydrate hydrolase-immobilized magnetic nanoparticle according to claim 1, wherein the carbohydrate hydrolase is cellulase.
6. The carbohydrate hydrolase-immobilized magnetic nanoparticle according to claim 1, which can be recycled by using magnetic field or filtration membrane.
7. A method of preparing ethanol from a graminaceous plant by using the carbohydrate hydrolase-immobilized magnetic nanoparticle according to claim 1, comprising:

(i) mixing buffer with a graminaceous plant to form a mixture;
(ii) placing the mixture into a bioreactor;
(iii) adding the carbohydrate hydrolase-immobilized magnetic nanoparticle into a bioreactor;
(iv) transferring the soluble hydrolysate into ethanol fermentor;
(v) adding ethanol fermentation yeast into the fermentor to produce ethanol, and
(vi) purifying ethanol by passing through molecule sieve.

8. The method according to claim 7, further comprises recycling the carbohydrate hydrolase-immobilized magnetic nanoparticle by using magnetic field or filtration membrane for next carbohydrate hydrolysis.

9. The method according to claim 7, wherein the graminaceous plant is rice straw.

10. The method according to claim 7, wherein the magnetic nanoparticle is $Fe_3O_4$.

11. The method according to claim 7, wherein the carbohydrate hydrolase is cellulase.

12. A continuous system of preparing ethanol, comprising:
(i) a bioreactor with filtration membrane, wherein the bioreactor comprises a carbohydrate hydrolase-immobilized magnetic nanoparticle according to claim 1 for decomposing high-molecular weight carbohydrate into oligosaccharide, and
(ii) an ethanol fermentor connected with bioreactor by connected pipe, wherein the ethanol fermentor comprises microorganism for producing ethanol.

13. The system according to claim 12, further comprises ethanol distillation tank connected with ethanol fermentor for ethanol production.

14. The system according to claim 12, further comprises magnetic field supplier to enhance the recycling of the carbohydrate hydrolase-immobilized magnetic nanoparticle.

15. The system according to claim 12, wherein the filtration membrane is used to separate the soluble hydrolysate and the carbohydrate hydrolase-immobilized magnetic nanoparticle and partially digested but insoluble rice straw particle by applying pressure.

16. The system according to claim 15, wherein the carbohydrate hydrolase-immobilized magnetic nanoparticle and partially digested but insoluble rice straw particle are recycled for next carbohydrate hydrolysis in a bioreactor.

17. The system according to claim 12, wherein connected pipe can transfer and autoclave the soluble hydrolysate simultaneously in situ from bioreactor to ethanol fermentor.

18. The system according to claim 12, wherein the magnetic nanoparticle is $Fe_3O_4$.

19. The system according to claim 12, wherein the carbohydrate hydrolase is cellulase.

20. The system according to claim 12, wherein the microorganism is yeast.

* * * * *